(12) United States Patent
Kawchuk (10) Patent No.: US 6,569,098 B2
(45) Date of Patent: May 27, 2003

(54) NON-INVASIVE DIAGNOSTIC METHOD AND APPARATUS FOR MUSCULOSKELETAL SYSTEMS

(75) Inventor: Gregory N. Kawchuk, Calgary (CA)

(73) Assignee: University Technologies International Inc., Calgary (CA)

( * ) Notice: Subject to any disclaimer, the term of this patent is extended or adjusted under 35 U.S.C. 154(b) by 0 days.

(21) Appl. No.: 09/808,035

(22) Filed: Mar. 15, 2001

(65) Prior Publication Data

US 2002/0103432 A1 Aug. 1, 2002

(30) Foreign Application Priority Data

Jan. 31, 2001 (CA) .............................. 2333224

(51) Int. Cl.[7] ................................ A61B 8/00
(52) U.S. Cl. ................. 600/437; 600/438; 600/587
(58) Field of Search .............. 600/437, 587, 600/594, 438, 471

(56) References Cited

U.S. PATENT DOCUMENTS

| | | |
|---|---|---|
| 4,762,134 A | 8/1988 | Gala |
| 4,852,397 A | 8/1989 | Haggag |
| 4,947,851 A | 8/1990 | Sarvazyan et al. |
| 5,101,835 A | 4/1992 | DelRe |
| 5,107,837 A | 4/1992 | Ophir et al. |
| 5,143,070 A | 9/1992 | Ophir et al. |
| 5,178,147 A | 1/1993 | Ophir et al. |
| 5,247,937 A | 9/1993 | Ophir et al. |
| 5,265,612 A | 11/1993 | Sarvazyan et al. |
| 5,293,870 A | 3/1994 | Ophir et al. |
| 5,433,215 A | 7/1995 | Athanasion et al. |
| 5,458,119 A | 10/1995 | Vanharanta |
| 5,474,070 A | 12/1995 | Ophir et al. |
| 5,524,636 A | 6/1996 | Sarvazyan et al. |
| 5,662,122 A | 9/1997 | Evans |
| 5,678,565 A | 10/1997 | Sarvazyan |
| 5,785,663 A | 7/1998 | Sarvazyan |
| 5,836,894 A | 11/1998 | Sarvazyan |
| 5,897,510 A | * 4/1999 | Keller et al. ................. 600/552 |
| 5,922,018 A | 7/1999 | Sarvazyan |

OTHER PUBLICATIONS

Kawchuk, Fauvel, Dmowski. Ultrasonic quantification of osseous displacements resulting from skin surface indentation loading of bovine para–spinal tissue. Clinical Biomechangics 15 (2000) 228–233, Jun. 2000.*

Kawchuk, et al.—A Non–Invasive Method of Quantifying Osseous Motion Within Para–Spinal Tissue Under Externally Applied Loads—Abstract—Proceedings of the International Society for the Study of the LIS—Jun., 1999.

Kawchuk, et al.—Ultrasonic Quantification of Osseous Displacements Resulting From Skin Surface Indentation Loading of Bovine Para–Spinal Tissue—Clin. Biomechanics 15 (2000) 228–233, Jun. 2000.

* cited by examiner

Primary Examiner—Francis J. Jaworski
Assistant Examiner—Ruby Jain
(74) Attorney, Agent, or Firm—Bennett Jones LLP (57) ABSTRACT

A system for determining displacement of an osseous target underlaying soft tissue assists in the diagnosis of disorders of the musculoskeletal system. The system includes an ultrasonic transducer/indenter which is used to compress the target tissue while concurrently obtaining ultrasound data. The displacement of the osseous target is determined by subtracting soft tissue compression from the overall displacement of the transducer/indenter. The transducer/indenter may be mechanically actuated or manually actuated.

6 Claims, 4 Drawing Sheets

NON-INVASIVE DIAGNOSTIC METHOD AND APPARATUS FOR MUSCULOSKELETAL SYSTEMS

FIELD OF THE INVENTION

The present invention relates to methods and apparatus which may assist in diagnosing disorders of the musculoskeletal system and in particular the spine.

BACKGROUND OF THE INVENTION

Joints of the human body permit movement through the contraction of muscular tissues acting on osseous structures (bones) which in turn are united by soft tissue linkages (ligaments). Imbalance in the relation between the rigidity and flexibility of a human joint has long been hypothesized to result in pathology and/or pain. Specifically, many musculoskeletal conditions such as hypermobility or osteoarthritis are thought to be characterized by excessive or insufficient displacements of osseous structures. While the relation between aberrant osseous motion and pathology/pain is plausible, the invasive and sometimes harmful nature of many investigative techniques has left the clinical significance of this relation incompletely understood.

Approaches which use extracted human tissues (in vitro) have described aberrant spinal kinematics in a number of pathological processes including disc degeneration[1,2]. While important, the clinical significance of these studies cannot be ascertained due to limitations of the in vitro process which include tissue loss, lack of tissue function and the inability to assess subjective phenomena (e.g. pain).

To resolve these limitations and address the issue of clinical significance, many investigative techniques have been employed that assess displacement of osseous structures in living humans. While use of existing in vivo techniques resolves several of these limitations, the majority are invasive and/or have the potential for harm which preclude their use in large populations. These techniques include surgical fixation[3,4] and two-dimensional radiographic imaging involving ionizing radiation[5–7].

For this reason, a limited number of in vivo techniques have been developed which are non-invasive[8–11]. Unfortunately, these techniques are considered to be highly variable due to (1) their dependency on instrumentation which attempts to relate skin movement with the displacements of underlying osseous structures and (2) their dependency on subject-generated movement to create the displacements they attempt to quantify. As a result, these non-invasive, in vivo techniques are incapable of direct quantification of spinal mechanics and/or performing controlled loading protocols.

Therefore, there is a need in the art for non-invasive methods and systems for diagnosing musculoskeletal disorders by measuring osseous displacement in response to a controlled load.

SUMMARY OF THE INVENTION

As a response to this need, the applicant has developed non-invasive methods and apparatuses that permit direct quantification of the displacement of a specific osseous structure in response to a pre-defined, externally applied load. This method, referred to herein as ultrasonic indentation (UI), is based on the principle that under an applied load, the displacement of a rigid target within a compressible medium can be determined by subtracting the resulting compression between the loading interface and the rigid target from the distance through which the load was applied ($d=A_a-A_{st}$, where d is the displacement of the rigid target, $A_a$ is the displacement of the object used to apply the indentation load and $A_{st}$ is the compression of the soft tissue between the interface of the indentation object and the indentation target).

In UI, an indentation load is applied to the external surface of the body by an ultrasonic transducer which is pressed bluntly into the soft tissues overlying the bone of interest either by hand or by mechanical actuation. The displacement of the ultrasonic transducer (Aa) is quantified by one of a variety of transducers located onboard the device itself. In the case of mechanical application of the indentation load, $A_a$ is quantified by a linear voltage displacement transducer or when applied by hand, remotely through a tracking device (optical, magnetic or inertial tracking). By obtaining data from ultrasonic waves reflected from a rigid, echogenic target (e.g. bone), the depth of the bone in relation to the position of the ultrasonic transducer may be determined. If this depth is quantified at the beginning and end of indentation loading, soft tissue compression (Ast) can be quantified by subtracting the depth of the bone found at maximal indentation from its depth at pre-indentation. The substitution of $A_a$ and $A_{st}$ values in the above equation results in the displacement of the rigid target in the plane of indentation (d).

The invention comprises both a method and apparatus. Accordingly, in one aspect of the invention, the invention comprises a diagnostic method of determining displacement of an osseous structure underlying soft tissue in response to an indenting force applied to the soft tissue and the osseous structure, comprising the steps of:

(a) providing an ultrasonic transducer/indenter having indenting surface;

(b) positioning the transducer/indenter over a target comprising the osseous structure underlying a layer of soft tissue;

(c) positioning the transducer/indenter in contact with the soft tissue, without substantially indenting the soft tissue;

(d) recording a first set of ultrasound data;

(e) moving the transducer towards the osseous structure while measuring the displacement of the transducer/indenter;

(f) recording a second set of ultrasound data;

(g) determining the soft tissue compression by comparing the first ultrasound data to the second ultrasound; and (h) subtracting the soft tissue compression from the total displacement of the transducer/indenter to determine osseous displacement.

In another aspect of the invention, the invention may comprise an apparatus for diagnosing a disorder of a musculoskeletal system by determining displacement of an osseous structure underlying soft tissue in response to a load, said apparatus comprising:

(a) a support frame;

(b) an electromechanical actuator attached to the frame and having a thrust tube;

(c) control means associated with the actuator for controlling movement and direction of movement of the thrust tube;

(d) an ultrasonic transducer/indenter mounted to the thrust tube;

(e) a load cell mounted between the thrust tube and transducer/indenter;

(f) a linear position transducer associated with the actuator for determining the displacement of the thrust tube;

(g) first processing means for analysing ultrasound data taken by the ultrasonic transducer/indenter and determining soft tissue thickness and changes in soft tissue thickness; and (h) second processing means operatively connected to the linear position transducer and to the first processing means for calculating osseous displacement from the displacement of the thrust tube and changes in soft tissue thickness.

In another aspect, the invention may comprise a system for diagnosing a disorder of a musculoskeletal system such as the spine by determining displacement of an osseous structure underlying soft tissue, in response to an indentation load, said apparatus comprising:

(a) a handheld ultrasonic transducer/indenter which produces and transmits ultrasonic derived data;

(b) a locator device associated with the transducer/indenter which communicates with a location sensor;

(c) means associated with the location sensor for determining the location of the transducer/indenter and for calculating the displacement of the transducer/indenter;

(d) a first processor adapted for receiving and analysing the ultrasound derived data and determining soft tissue thickness and changes in soft tissue thickness; and (e) a second processor operatively connected to the first processor and the location determining means, said second processor adapted for calculating osseous displacement from the displacement of the transducer/indenter and changes in soft tissue thickness.

The processing means or processors referred to herein may include a general purpose computer programmed with appropriate software, or programmable firmware or a programmed logic controller or other hardware or software known to those skilled in the art.

BRIEF DESCRIPTION OF THE DRAWINGS

The invention will now be described by way of exemplary embodiments with reference to the accompanying simplified, diagrammatic, not-to-scale drawings. In the drawings:

FIGS. 4A and 4B are ultrasound images taken during the ultrasonic indentation method of the present invention. FIG. 4A shows the image at minimal indentation (1N load) and FIG. 4B shows the image at maximal indentation (70N).

DETAILED DESCRIPTION OF THE INVENTION

Measurement of osseous displacement by ultrasonic indentation provides useful and clinically significant information. Such measurements may permit the discrimination between normal and pathologic biomechanics of a variety of musculoskeletal systems. The present invention may have particular application to the vertebral column, however, it may be applied usefully to any musculoskeletal system in the human body. When describing the present invention, the following terms have the following meanings, unless indicated otherwise. All terms not defined herein have their common art-recognized meanings.

A. Definitions

The term "ultrasonic transducer" refers to a device that converts inaudible high frequency sound, or mechanical vibration, to an electrical voltage or signal and/or vice versa.

The term "transducer/indenter" refers to an ultrasonic transducer probe which is used to apply a physical force to the musculoskeletal system at the same time the probe collects ultrasonic data.

B. Description

In one aspect, the invention comprises in vivo application of ultrasonic indentation to a rigid osseous target beneath a soft tissue covering. An indentation load is applied to the indentation target by an ultrasonic transducer/indenter. The change in soft tissue thickness during indentation loading may be measured by the ultrasound data generated by the transducer/indenter and compared to the overall displacement of the transducer/indenter. The overall displacement of the transducer consists of the displacement of the osseous target plus the compression of the soft tissue overlying the target.

1. Determination of Displacement of Applied Load (Aa)

If the total displacement or movement of the transducer/indenter is known, then the displacement of the underlying osseous structure is calculated as the total displacement less the change in soft tissue thickness.

Figure 1:
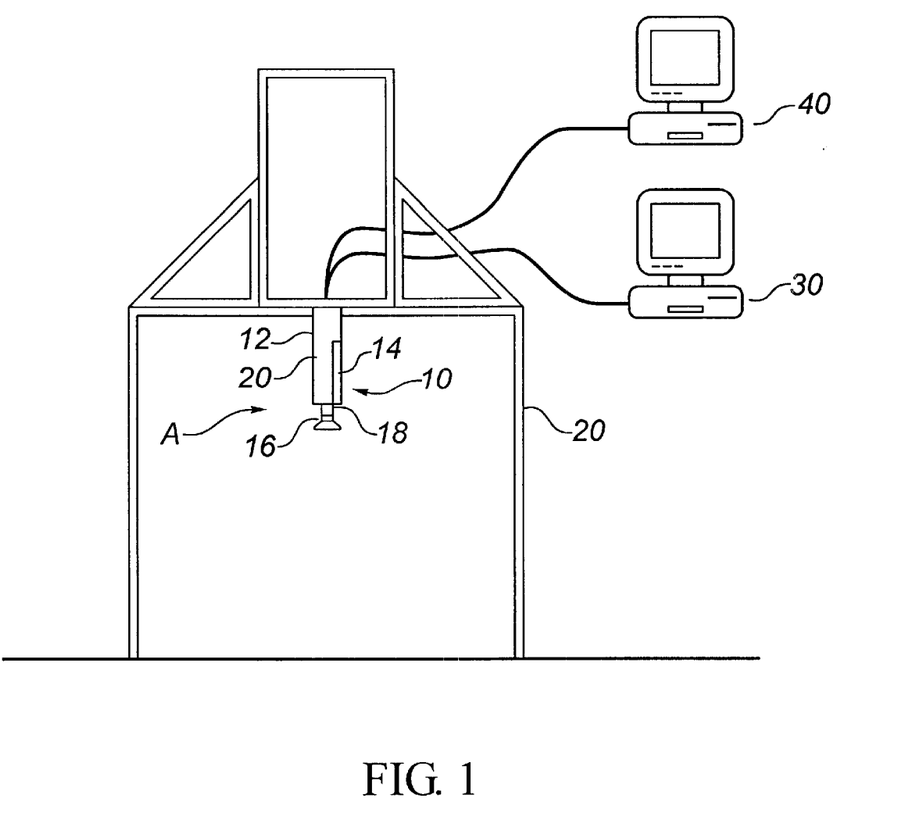
FIG. 1 is a schematic representation of a mechanically actuated ultrasonic indentation apparatus.
Figure 2:
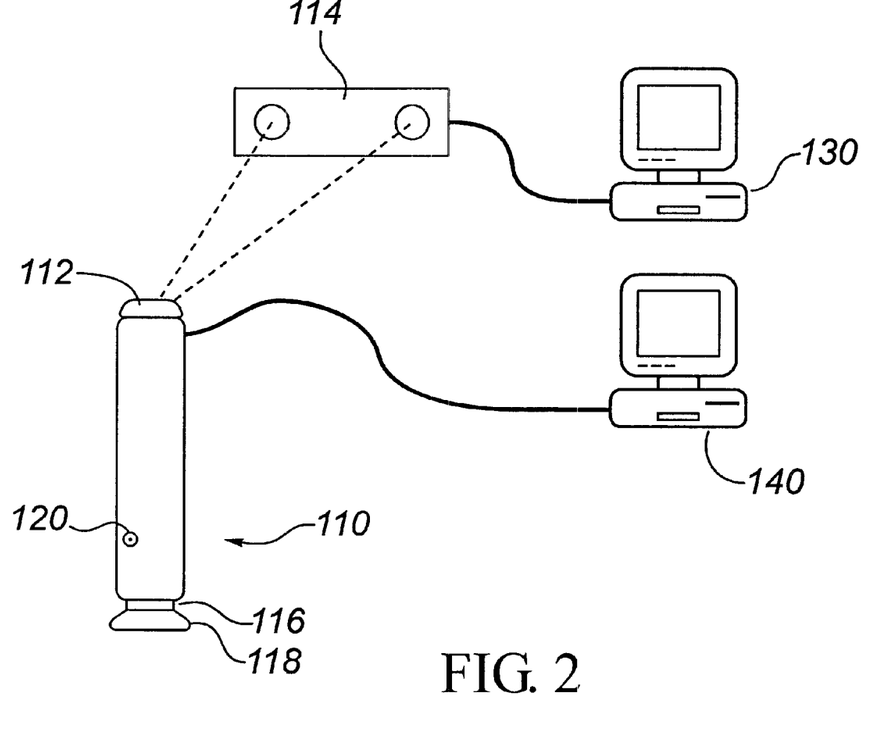
FIG. 2 is a schematic representation of a manually actuated ultrasonic indentation apparatus.
Figure 3:
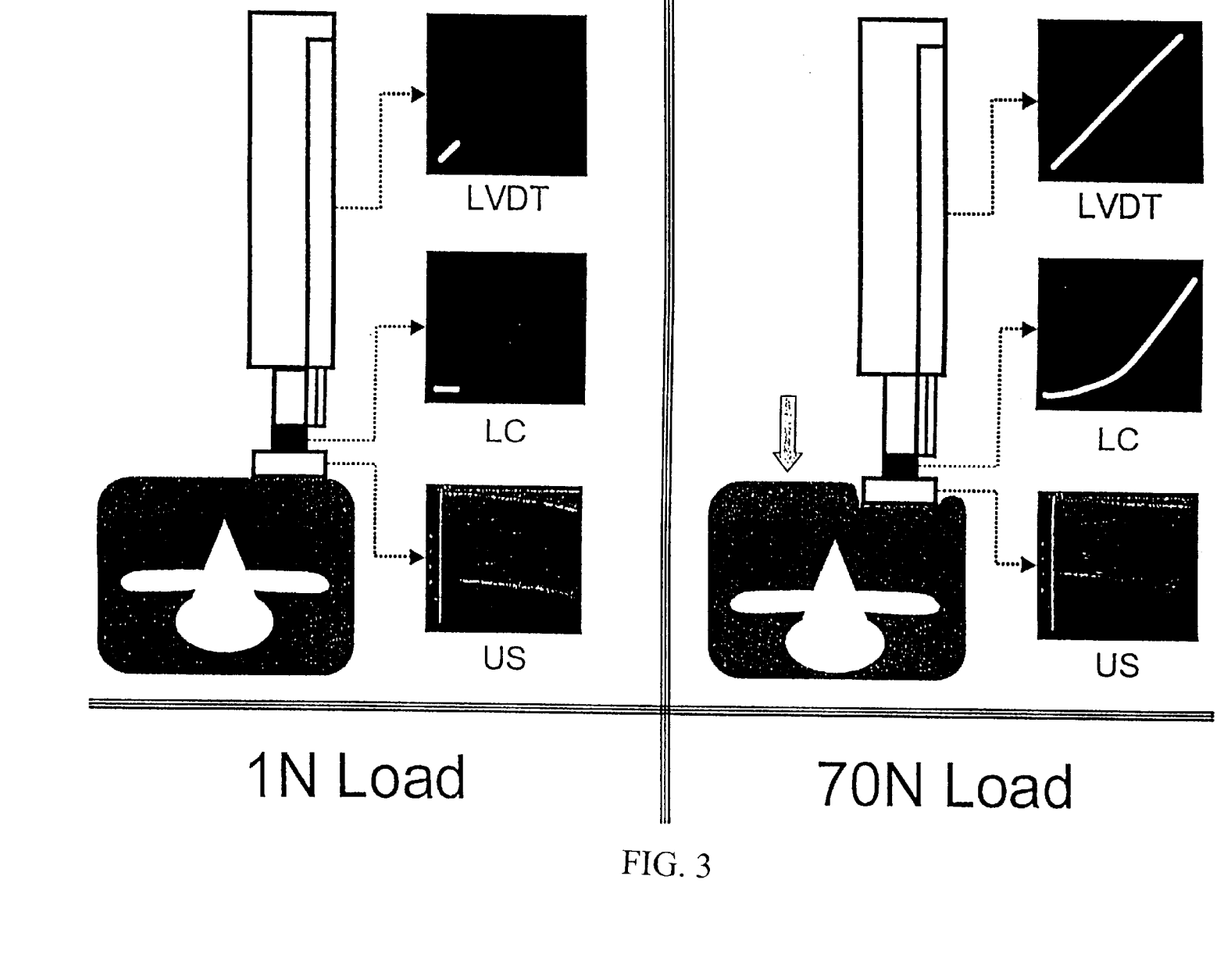
FIG. 3 is a representation of an indentation load being applied to a vertebrae and the measurements taken by the linear voltage displacement transducer, load cell and ultrasound.

The overall displacement of the transducer/indenter may be determined by fixing the housing (12) of the transducer/indenter (10) in space and using means such as a linear voltage displacement transducer (14) to measure overall displacement of the transducer/indenter (10) itself, as is shown in FIG. 1. In another embodiment, the overall displacement of the transducer/indenter (110) may be quantified by a positional location device (112) located on transducer/indenter (110) itself which communicates with a location sensor (114) either by wired or wireless means, as is shown in FIG. 2.

In practice, the clinician may assess a patient in the any number of orientations (prone, supine, sitting, upright etc) as long as the patient is braced or restrained rigidly against the direction of the applied indentation load. The direction of the applied load is preferably aligned with the direction of the osseous displacement which is to be tested. For example, the method may be practiced to determine vertebral displacement to a load which is perpendicular to the horizontal plane of the spinal column, assuming the patient is prone. Generally, the load applied by the transducer/indenter will be perpendicular to the skin surface at the target area. However, there may be instances where the load is applied at an angle which is not perpendicular to the skin surface, depending on the osseous structure which is being displaced.

2. Determination of Soft Tissue Compression (Ast) From Ultrasonic Data

Figure 4A:
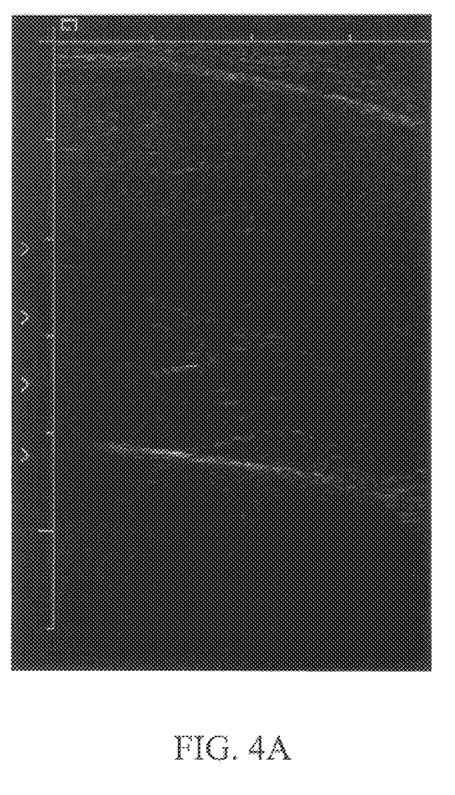
Figure 4B:
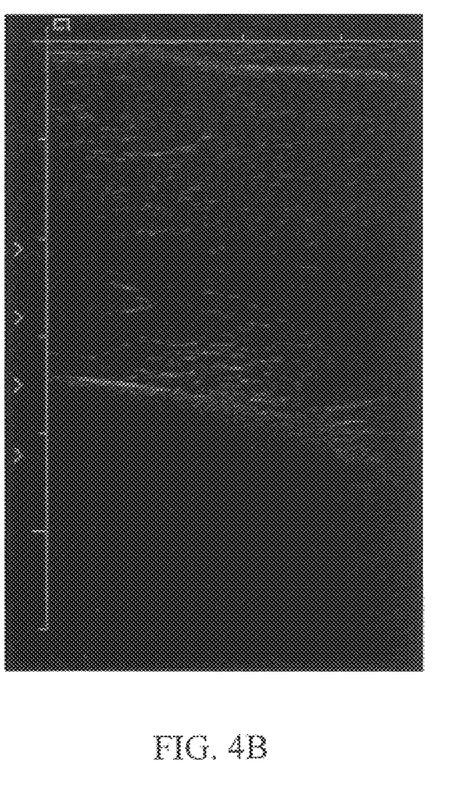

In one embodiment, the ultrasound transducer/indenter may be a "B" mode transducer, which produces two-dimensional ultrasonic images as shown in FIG. 4. These images can be collected continuously during indentation loading or at just at the minimal and maximal applied loads. Edge detection algorithms, which are well known in the art, may be used to determine the number of image pixels between the ultrasonic transducer/skin interface and the echogenic surface of the osseous target in closest proximity to the ultrasonic transducer at any time during indentation. The resulting number of pixels may be converted to a physical measurement of distance by dividing the imaging depth of the transducer by the number of pixels observed to occur over that distance. For example, if a transducer has an imaging depth of 60 mm displayed over 360 vertical pixels, then the imaging resolution is 0.1899 mm/pixel. A distance of 10 pixels as determined by the edge detection algorithms would then translate into a distance of 1.899 mm.

In an alternative embodiment, the soft tissue thickness may be estimated by the use of an A-mode ultrasonic transducer. In this ultrasonic mode, two-dimensional images are replaced with graphical ultrasonic data which represents the time required for the ultrasonic wave, travelling through the soft tissue at a specific speed, to reach the reflective osseous tissue and then return to the transducer (distance along the x-axis). The strength or intensity of the reflected wave is represented as the height of the signal along the y-axis. As the speed of ultrasonic waves in soft tissue can be obtained in advance of testing by a variety of procedures known in the art, or may be selected from textbook values, the distance to the osseous target from the transducer may be determined by the relation distance=speed×time. Although ultrasonic waves may reflect from a variety of tissue targets, reflections from the osseous target (bone) are usually several more times intense than those from other softer targets such as muscle or fat. Therefore, peak-detection algorithms, which are well known in the art, can be used be used to determine the most intense peak within the A-mode graphical data. This peak location will then correspond to the distance of that object from the ultrasonic transducer. With this information, the depth of the osseous target can be quantified at any time during indentation loading and the displacement of the osseous object quantified.

3. UI Apparatus

In one embodiment shown in FIG. 1, the ultrasonic indentation apparatus (A) comprises a transducer/indenter (10) which is serially mounted to a load cell (16), a thrust tube (18) and a linear position transducer (14). The thrust tube is connected to an electromechanical actuator (20) which moves the thrust tube and therefore the transducer/indenter. The linear position transducer (14) registers the displacement of the indenter. As long as the apparatus (A) is maintained in a constant spatial relationship with the patient, the measurement of total displacement of the transducer/indenter (Aa) may be accurately measured.

In operation, the transducer is lowered until it contacts the soft tissue surface of the patient, over the vertebral target, and an initial ultrasound image is taken at a position where the load cell (16) registers a minimal force of about 1 N. This pre-loading is preferred as it eliminates any space between the indenter and the skin surface which would cause an erroneous measure. The transducer/indenter is then moved downwards by the thrust tube until a predetermined maximal force, 70 N for example, is reached and a second ultrasound image is taken at that point. The change in soft tissue thickness and the overall displacement registered by the linear position transducer are recorded and used to calculate displacement of the vertebral segment as described above.

The load cell (16) is a preferred but not essential element in the apparatus of the present invention. It permits relatively precise application of a known amount of force. However, the apparatus and method described herein may function without the load cell.

The apparatus (A) is preferably mounted to a support frame (20) which may itself be mounted to the table or platform on which the patient is placed or which may be self-supporting as is shown in FIG. 1. The support frame (20) fixes the frame of reference by which overall displacement of the transducer/indenter is determined.

The apparatus may be controlled using a programmed logic controller or a general purpose computer (30) programmed to receive and process the outputs from the linear position transducer, the load cell and to control the actuator. The control means (20) may also receive the values necessary to calculate the soft tissue compression and vertebral displacement.

As well, conventional ultrasound displays (40) may be provided to concurrently visualize the ultrasound data being recorded by the ultrasound transducer/indenter. It may be possible to combine the ultrasound display processing and control and calculation algorithm processing in one processing unit.

The apparatus may be controlled to take the second ultrasound image or measurement by specifying the maximal load registered by the load cell or by specifying the maximal overall displacement of the actuator. In the example given below, a maximal force of 70 N was chosen as the point where a second ultrasound image was taken and where the actuator reversed to decompress the vertebral target.

In an alternative embodiment, as shown in FIG. 2, the indentation force by the transducer/indenter (110) is applied manually and the movement of the transducer/indenter (110) is measured by means of an appropriate position location device (112) and location sensor (114). In this case, a handheld transducer/indenter (110) is provided which may be manipulated directly by a user and which includes means to determine and track the transducer's spatial position. The same principles of determining osseous displacement as described above apply in this embodiment except that displacement of the indenter (Aa) is determined by remote sensing means. The handheld transducer/indenter may communicate with a central processing means (130), which may preferably be a general purpose computer, by cable or by wireless means. In one embodiment, the transducer/indenter may take the form of a rigid wand (110) contoured to fit the hand ergonomically. The wand may be held in a single hand and used to apply a blunt indentation load to tissues overlaying an osseous target such as a single vertebra. Specifically a load cell (116) and ultrasonic transducer (118) are mounted in series to one end of the wand and a position location device (112) to the wand, preferably the other end. The load cell (116) may be any electronic or mechanical device capable of quantifying the amount of force applied to the tissue during indentation loading. The ultrasonic transducer may be any form or mode (A or B) that would be capable of quantifying the depth of an echogenic structure such as bone underlying human soft tissue (i.e. bone).

The position location device and sensor (112, 114) may be an electrical or mechanical device capable of determining the position or orientation of the wand in three-dimensional space. Such positioning devices are well known in the art. For example, such positioning devices may include reflective or electronic marker (112) systems placed on the wand with stationary optical cameras (114), such as the Polaris™ optical tracking system manufactured by Northern Digital Inc. (www.ndigital.com/polaris.html). Such optical technology may be described in U.S. Pat. Nos. 5,828,770, 5,923,417 and 6,061,644, the contents of which are incorporated herein by reference. Alternatively, the positioning devices may include magnetic emitters (112) placed on the wand with a stationary magnetic sensor (114), such as the laserBIRD™ or 3D-BIRD™ systems manufactured by Ascension Technology Corporation (www.ascension-tech.com). Other useful systems may be used such as inertial/ultrasonic transducers placed on the wand itself which transmit position data, such as the IS900™, IS600™ or IS300™ systems manufactured by Intersense (www.isense.com).

Suitable position location devices may also be described in U.S. Pat. Nos. 5,592,401, 5,645,077, 5,807,284, 5,916,181, 5,930,741, 5,953,683, 5,971,976, 6,048,324, 6,054,951, 6,122,538 and 6,162,191, the contents of which are incorporated herein by reference.

Each of the load cell (116) and position location device (112) communicates with a computer (130) and its associated software directly or by wireless means. The ultrasonic transducer (118) may communicate with an ultrasound processor and display (140) by direct or wireless means. Together, these three wand-based devices are used to determine the displacement of an underlying osseous target in response to an applied indentation load as described previously. A finger-controlled micro-switch (120) placed on the wand (110) may be provided and used by the operator to control the on-board instrumentation and data collection.

The wand operator may perform ultrasonic indentation of a soft tissue in the following manner. The operator would set the wand vertically upright on a horizontal, rigid surface with the ultrasonic transducer contacting the surface. The outputs of all three electronic/mechanical devices would then be 'zeroed' by the computer used for data visualization/collection. The wand operator may then apply an acoustic coupling agent to the tissue surface of interest and allow the ultrasonic end of the wand to rest gently on the tissue surface while supporting the wand itself. The operator would view the nearby computer screen (140) to observe either graphical or image-based ultrasonic output to locate the osseous target and therefore the indentation site of choice.

Once the indentation site is located, the operator may then view another computer display which charts the three-dimensional position of the wand. Alternatively, if a single computer is used to process the ultrasound data and the wand position data, the user may change the view on the computer monitor to a second display which permits visualization of the three-dimensional position of the wand. Such a switch may be accomplished by a trigger or switch located on the wand itself. Alternatively, the first and second displays may be viewed concurrently in separate windows or monitors.

The position of the wand may be displayed graphically with respect to a target which would represent the desired wand position as defined by the user (including user-defined tolerances). Once the position and orientation of the wand was determined to be satisfactory (e.g. overlying and perpendicular to the target), the operator may then begin the data collection sequence. The operator would then begin to indent the tissue while a continual display of wand position and rate of indentation would be displayed to the operator with respect to user-defined target values and tolerances. When the indentation load would reach a first user-determined magnitude (pre-load), the system may give off a signal such as an audible beep, signalling the user to pause at this load while the computer collected data from the wand devices. The operator would maintain this load based on the graphical/target display. At the completion of the data collection period, another signal may then be provided, signalling the user to indent the tissue to a second, larger load magnitude (max-load).

As with the calculation described previously, ultrasonic data collected at the pre-load and max-load would be used to determine the magnitude of tissue compression during indentation (Ast). Data from the positioning system collected between the pre-load and max-load would then be used to determine the distance over which the wand was applied (Aa) for the desired angle of indentation (Ws). Data from the positioning system may then also be used following the indentation itself to display the variation in wand angle with respect to Ws, the variation in the rate of load application between pre- and max-loads and the variability of the pre- and max-loads. These data could then be used to determine the overall variability of the indentation process. Based on the user-defined tolerances for wand orientation, indentation rate and load stability, the above data could be as a measure of quality control for the indentation process itself.

C. EXAMPLE

The following example is intended to be illustrative of the claimed invention but not limiting in any manner.

Eight of sixteen domestic pigs (Swedish Landrace) were selected at 3 months of age to undergo a surgical procedure known to cause lumbar disc degeneration through direct endplate injury[14]. Following surgery, each animal recuperated in an animal facility and was monitored daily for a period of four months.

At the end of four months, all eight animals having undergone endplate surgery were collected for biomechanical and surgical testing in addition to the remaining eight age-matched control animals. Each animal was separately sedated then anaesthetized. Biomechanical (indentation loading) procedures were then performed.

Ultrasonic Indentation Equipment

Following animal preparation, ultrasonic indentation equipment (FIG. 1) was positioned over each prone animal (mechanical embodiment)[15]. This equipment consisted of a load cell transducer (Load Cell Central, Monroeton Pa., U.S.A) and a 7 MHz linear array ultrasonic transducer/indenter (Acuson, Mountainview, Calif., U.S.A.) mounted in-series to the terminal end of an electromechanical linear actuator (18) (Industrial Devices Corporation, Petaluma, Calif., U.S.A). These two transducers were used during indentation to measure applied load and to image subsurface echogenic anatomy respectively. A linear displacement transducer attached in-parallel quantified the actuator displacement. The actuator/transducer complex (A) was suspended in an aluminum support frame that allowed the apparatus to be translated horizontally and angulated vertically, while the frame itself could be restrained against the surgical table by an array of four detentes. Electronic and mechanical safety mechanisms permitted premature cessation and immediate reversal of actuation by the operator. Voltage signals related to indentation load and actuator displacement were acquired by a single analog-to-digital board (National Instruments, Austin, Tex., U.S.A). Customized software (National Instruments, Austin, Tex., U.S.A) permitted data collection and concurrent generation of actuator control signals. So that appropriately rapid control signals could be sent to the actuator, a sampling/control rate of 1 kHz was selected.

Ultrasonic Indentation

For all indentation trials, each anesthetized animal was placed prone in a support that restricted gross body movement. The base of the indenter equipment was then locked against this support by four horizontal detentes. In each animal, the indentation site was designated to be the mid-point of the right transverse process of L4 which was located by applying ultrasonic coupling gel to the ultrasonic transducer then lowering the transducer toward the animal's back until an image was obtained. The ultrasonic transducer was then moved in the horizontal plane until the target location was identified[16]. Once located, the position of the actuator/transducer was locked and the ultrasound transducer was raised to approximately 5 cm above the tissue surface. Indentation then proceeded vertically downward at a rate of 2.5 mm/s until a load of 1 N was attained. During indentation, the respiratory effort of each animal was maintained in a static state for a period of approximately 10 seconds through removal of the main hose from the ventilator. At a 1 N load, indentation was paused for approximately 3 seconds and an ultrasonic image collected. All ultrasonic images were obtained as 0.31 megapixel images (640×480 pixels) at an imaging depth of 60 mm and a focal depth optimized to each animal's transverse process. After the application of a 1N load for 3 s, indentation was allowed to proceed at the same rate to a maximal load of 70 N. At maximal load, indentation was paused for another 3 seconds and a second ultrasonic image was collected. The direction of indentation was then reversed to return the ultrasound transducer to its pre-indentation position. A minimum of four trials was collected in this manner at 120 s intervals.
Determination of Vertebral Displacement.

Vertebral displacement as a result of indentation loading was calculated by the following procedure. Transducer-to-bone tissue thickness in pre-indentation and maximal indentation ultrasonic images was determined by a visually-based, edge-detection algorithm. The difference between these values was calculated and then subtracted from the change in indenter displacement over the same time period. Each measure of displacement was then normalized to the animal's body weight and soft tissue thickness as determined from the 1N image.

FIG. 4 displays two ultrasonic images taken from the same animal demonstrating the posterior cortex of the transverse process of L4 in a cross sectional image of the trunk following the application of a 1 N load and 70N load. The average vertebral displacement for the control group was 18.69 mm, (SE 0.84) and 16.39 mm (SE 0.85) for the degenerative group. Receiver Operating Curve analysis of vertebral displacement measures between control and experimental groups demonstrated a sensitivity, specificity and diagnostic accuracy of 75.0% (CI 35.0–96.1), 83.3% (CI 36.1–97.2) and 77.1% (CI 51.4–100.0) respectively.

The magnitude of posteroanterior vertebral displacement during indentation loading was quantified ultrasonically in a group of experimental animals and a group of matched controls. The diagnostic accuracy of vertebral displacement measures between animal groups was greater than chance.

The vertebral displacements of the degenerative animals as a group were less than the control group. This observation is consistent with other invasive studies which describe a decrease in posteroanterior vertebral motion and/or increased stiffness in degenerated segments[20,23]. Specifically, diagnostic accuracy distinguished between control and experimental groups of animals at levels greater than chance as their confidence intervals did not bound 50%. Diagnostic performance data from UI were equal or superior to a number of techniques (invasive or otherwise) used clinically to assess arthritic change in the spine. It should be noted that many of these comparative techniques involve use of ionizing radiation and maximize their diagnostic performance by a) accepting any pathological change as a positive[24], b) using a spectrum of tests rather than a single test[25], b) using a "gold standard"[25,26] shown to have low specificity[24], or d) through the use of chronic disease states. Comparatively, vertebral measures derived from UI were not combined with other outcomes and were obtained relatively quickly with respect to the condition's pathogenesis (approximately 4 months following initiation). Additionally, the disease condition present in this study was not diagnosed from a random population but was a surgically induced injury whose location and effect was confirmed by dissection.

As a result of these observations, it was concluded that UI-derived measures of vertebral displacement are clinically significant and possess the additional advantages of being objective and non-invasive. It is surmised that UI has potential as a technique capable of providing relevant data pertaining to disorders that affect the mechanics of the spine As will be apparent to those skilled in the art, various modifications, adaptations and variations of the foregoing specific disclosure can be made without departing from the scope of the invention claimed herein.

REFERENCES

The following references are referred to above as superscript numerals and the contents of each reference are incorporated herein as if reproduced in their entirety within this specification.

1. Mimura M, Panjabi M M, Oxland T R, Crisco J J, Yamamoto I, Vasavada A. Disc degeneration affects the multidirectional flexibility of the lumbar spine. Spine 1994;19:1371–80.
2. Nachemson A L, Schultz A B, Berkson M H. Mechanical properties of human lumbar spine motion segments. Influence of age, sex, disc level, and degeneration. Spine 1979;4:1–8.
3. Kaigle A M, Pope M H, Fleming B C, Hansson T. A method for the intravital measurement of interspinous kinematics. J Biomech 1992;25:451–6.
4. Steffen T, Rubin R K, Baramki H G, Antoniou J, Marchesi D, Aebi M. A new technique for measuring lumbar segmental motion in vivo. Method, accuracy, and preliminary results. Spine 1997;22:156–66.
5. Pearcy M, Portek I, Shepherd J. The effect of low-back pain on lumbar spinal movements measured by three-dimensional X-ray analysis. Spine 1985;10:150–3.
6. Dvorak J, Panjabi M M, Chang D G, Theiler R, Grob D. Functional radiographic diagnosis of the lumbar spine. Flexion-extension and lateral bending. Spine 1991; 16:562–71.
7. Okawa A, Shinomiya K, Komori H, Muneta T, Arai Y, Nakai O. Dynamic motion study of the whole lumbar spine by videofluoroscopy. Spine 1998;23:1743–9.
8. Russell P, Pearcy M J, Unsworth A. Measurement of the range and coupled movements observed in the lumbar spine. Br J Rheumatol 1993;32:490–7.
9. McGregor A H, Cattermole H R, Hughes S P. Spinal motion in lumbar degenerative disc disease. J Bone Joint Surg Br 1998;80:1009–13.
10. Madson T J, Youdas J W, Suman V J. Reproducibility of lumbar spine range of motion measurements using the back range of motion device. J Orthop Sports Phys Ther 1999;29:470–7.
11. Latimer J, Goodsel M M, Lee M, Maher C G, Wilkinson B N, Moran C C. Evaluation of a new device for measuring responses to posteroanterior forces in a patient population, Part 1: Reliability testing. Phys Ther 1996;76:158–65.
12. Kawchuk G, Elliott P. Validation of displacement measurements obtained from ultrasonic images during indentation testing. Ultrasound Med Biol 1998;24:105–11.
13. Kawchuk G, Fauvel O, Dmowski J. Ultrasonic quantification of osseous displacements resulting from skin surface indentation loading of bovine para-spinal tissue. Clin Biomech 2000; 15:228–233.
14. Holm S, Kaigle A, Ekstrom L, Hansson T. Degenerative properties of the porcine intervertebal disc due to endplate injury. In: 26th Annual Meeting of the International Study of the Lumbar Spine. Kona, Hi.; 1999. p. 183A.
15. Kawchuk G, Fauvel O, Dmowski J. Ultrasonic Indentation (UI): A procedure for noninvasive quantification of osseous displacements and bulk tissue properties. J Manipulative Physiol Ther 2000; In Press.
16. Kawchuk G, Fauvel O. Sources of variation in spinal indentation testing: indentation anxiety, intra-abdominal pressure, subject movement, indentation site relocation, and stiffness estimation. J Manipulative Physiol Ther 2000; In Press.
17. Penning L, Wilmink J T, van Woerden H H. Inability to prove instability. A critical appraisal of clinical-radiological flexion-extension studies in lumbar disc degeneration. Diagn Imaging Clin Med 1984;53:186–92.
18. Tanz S. Motion of the lumbar spine: A roentgenologic study. AJR 1953;69:399–412.
19. Pearcy M, Portek I, Shepherd J. Three-dimensional x-ray analysis of normal movement in the lumbar spine. Spine 1984;9:294–7.
20. Dvorák J, Panjabi M M, Novotny J E, Chang D G, Grob D. Clinical validation of functional flexion-extension roentgenograms of the lumbar spine. Spine 1991;16:943–50.
21. Quint U, Wilke H J, Shirazi-Adl A, Parnianpour M, Löer F, Claes L E. Importance of the intersegmental trunk muscles for the stability of the lumbar spine. A biomechanical study in vitro. Spine 1998;23:1937–45.
22. Wilke H J, Wolf S, Claes L E, Arand M, Wiesend A. Stability increase of the lumbar spine with different muscle groups. A biomechanical in vitro study. Spine 1995;20:192–8.
23. Kaigle A, Ekström L, Holm S, Rostedt M, Hansson T. In vivo dynamic stiffness of the porcine lumbar spine exposed to cyclic loading: influence of load and degeneration. J Spinal Disord 1998;11:65–70.
24. Rothschild B, Poteat G, Williams E, Crawford W. Inflammatory sacroiliac joint pathology: evaluation of readiologic assessment techniques. Clin Exper Rheum 1994;12:267–274.
25. Mau W, Zeidler H, Mau R, Majewski A, Freyschmidt J, Stangel W, et al. Evaluation of early diagnostic criteria for ankylosing spondylitis in a 10 year follow-up. Z Rheumatol 1990;49:82–7.
26. Gran J T. An epidemiological survey of the signs and symptoms of ankylosing spondylitis. Clin Rheumatol 1985;4:161–9.

What is claimed is:

1. A diagnostic method of determining displacement of an osseous structure underlying soft tissue in response to an indenting force applied to the soft tissue and the osseous structure, comprising the steps of:
   (a) providing an ultrasonic transducer/indenter having indenting surface;
   (b) positioning the transducer/indenter over a target comprising the osseous structure underlying a layer of soft tissue;
   (c) positioning the transducer/indenter in contact with the soft tissue;
   (d) recording a first set of ultrasound data;
   (e) moving the transducer towards the osseous structure while measuring the displacement of the transducer/indenter;
   (f) recording a second set of ultrasound data;
   (g) determining the soft tissue compression by comparing the first ultrasound data to the second ultrasound data; and
   (h) subtracting the soft tissue compression from the total displacement of the transducer/indenter to determine osseous displacement.

2. The method of claim 1 wherein the ultrasonic transducer is a "B" mode transducer and soft tissue compression is determined by the following steps:
   (a) determining a vertical resolution of the ultrasound images in units of length per pixel;
   (b) detecting an upper edge and a lower edge of the soft tissue in the first set of ultrasound data and in the second set of ultrasound data and determining a difference in thickness as a number of pixels; and
   (c) converting the difference in thickness in pixels to units of length.

3. The method of claim 1 wherein the ultrasonic transducer is an "A" mode transducer which produces an ultrasonic wave which passes through the soft tissue with a known speed and soft tissue compression is determined by determining a thickness of the soft tissue in the first set of ultrasound data and in the second set of ultrasound data by measuring a length of time required for an ultrasound wave to pass through the soft tissue, reflect off the osseous target and return to the transducer and multiplying by the speed of the ultrasonic wave in the soft tissue.

4. The method of claim 1 wherein the ultrasound transducer operates at a frequency between 5 MHz and 7 MHz.

5. The method of claim 1 wherein the ultrasonic transducer/indenter is moved by mechanical means.

6. The method of claim 1 wherein the ultrasonic transducer/indenter is handheld and moved manually.

* * * * *